United States Patent
Makino

(10) Patent No.: US 11,521,319 B2
(45) Date of Patent: Dec. 6, 2022

(54) ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 223 days.

(21) Appl. No.: 16/962,676

(22) PCT Filed: Feb. 4, 2019

(86) PCT No.: PCT/JP2019/003851
§ 371 (c)(1),
(2) Date: Jul. 16, 2020

(87) PCT Pub. No.: WO2019/156022
PCT Pub. Date: Aug. 15, 2019

(65) Prior Publication Data
US 2020/0364866 A1  Nov. 19, 2020

(30) Foreign Application Priority Data

Feb. 7, 2018 (JP) .............................. JP2018-020026

(51) Int. Cl.
| | |
|---|---|
| G06T 7/00 | (2017.01) |
| G06T 7/11 | (2017.01) |
| G06T 7/90 | (2017.01) |
| A61B 1/00 | (2006.01) |
| A61B 5/00 | (2006.01) |
| A61B 1/05 | (2006.01) |

(Continued)

(52) U.S. Cl.
CPC ........ *G06T 7/0014* (2013.01); *A61B 1/00045* (2013.01); *A61B 5/489* (2013.01);
(Continued)

(58) Field of Classification Search
None
See application file for complete search history.

(56) References Cited

U.S. PATENT DOCUMENTS

2009/0202124 A1  8/2009  Matsuda et al.
2012/0237122 A1  9/2012  Hirota et al.
(Continued)

FOREIGN PATENT DOCUMENTS

JP  2002-291733  10/2002
JP  2005192880 A  *  7/2005
(Continued)

OTHER PUBLICATIONS

Official Communication issued in International Bureau of WIPO Patent Application No. PCT/JP2019/003851, dated Apr. 16, 2019.

*Primary Examiner* — Gandhi Thirugnanam
(74) *Attorney, Agent, or Firm* — Greenblum & Bernstein, P.L.C.

(57) ABSTRACT

An endoscope system includes a processor including an image processing unit that obtains an inflammation evaluation value in which a degree of inflammation of a biological tissue is digitized on the basis of information of a color component of an image of the biological tissue, from the image that is obtained by imaging the biological tissue, and a monitor displaying the inflammation evaluation value. The image processing unit includes a blood vessel region determination unit obtaining certainty of a blood vessel region of the biological tissue in the image, a pixel evaluation value generation unit obtaining a pixel evaluation value by performing digitization processing with respect to each of the pixels of the image, a pixel evaluation value adjustment unit calculating an adjustment value in which the pixel evaluation value is reduced as the certainty of the blood vessel region increases.

9 Claims, 10 Drawing Sheets

(51) Int. Cl.
*A61B 1/06* (2006.01)
*A61B 1/07* (2006.01)

(52) U.S. Cl.
CPC .................. *G06T 7/11* (2017.01); *G06T 7/90* (2017.01); *A61B 1/00006* (2013.01); *A61B 1/05* (2013.01); *A61B 1/0669* (2013.01); *A61B 1/07* (2013.01); *G06T 2207/10024* (2013.01); *G06T 2207/10068* (2013.01); *G06T 2207/20224* (2013.01); *G06T 2207/30096* (2013.01); *G06T 2207/30101* (2013.01)

(56) References Cited

U.S. PATENT DOCUMENTS

| | | | | |
|---|---|---|---|---|
| 2014/0257114 | A1* | 9/2014 | Hirota | A61B 1/041 600/476 |
| 2015/0092993 | A1* | 4/2015 | Kanda | G06T 7/0012 382/106 |
| 2015/0356369 | A1 | 12/2015 | Kitamura et al. | |
| 2018/0279866 | A1* | 10/2018 | Makino | A61B 1/07 |
| 2019/0192048 | A1* | 6/2019 | Makino | A61B 5/00 |
| 2019/0273840 | A1* | 9/2019 | Makino | G06T 1/00 |
| 2020/0364866 | A1* | 11/2020 | Makino | G06T 7/11 |
| 2021/0133974 | A1* | 5/2021 | Makino | G06T 7/11 |
| 2021/0279498 | A1* | 9/2021 | Makino | G06V 10/56 |

FOREIGN PATENT DOCUMENTS

| | | |
|---|---|---|
| JP | 2008-093172 | 4/2008 |
| JP | 2010-184057 | 8/2010 |
| JP | 2012-192051 | 10/2012 |
| JP | 2013-111125 | 6/2013 |
| JP | 2013-255656 | 12/2013 |
| JP | 2014-161672 | 9/2014 |
| WO | 2017/057680 | 4/2017 |

* cited by examiner

ENDOSCOPE SYSTEM

TECHNICAL FIELD

The present invention relates to an endoscope system performing image processing with respect to an image of a biological tissue in a body cavity.

BACKGROUND ART

A lesion portion, for example, an inflamed site, in general, exhibits a color different from that of a normal mucosal membrane tissue. In accordance with the improvement of the performance of a color endoscope device, it is possible to identify the lesion portion such as an inflamed site of which the color is slightly different from that of a normal tissue. However, in order to enable an operator to identify the normal portion and the lesion portion by a slight color difference included in an endoscope image, it is necessary for the operator to receive long-term training under the guidance of a skilled person. In addition, it is not easy for even a skilled operator to identify the lesion portion from a slight color difference, and a cautious operation is required. Therefore, in an endoscope system, it is preferable to output a stable inflammation evaluation value that is capable of accurately evaluating the lesion portion, for example, the degree of inflammation of the inflamed site.

In response, an endoscope system is known in which a stable evaluation value can be calculated by suppressing a variation in an evaluation value of an inflamed site due to the brightness of an image, and a processing load for calculating the evaluation value can be suppressed (Patent Literature 1).

CITATION LIST

Patent Literature

Patent Literature 1: WO 17/057680 A

SUMMARY OF INVENTION

Technical Problem

The endoscope system described above includes a light source device applying illumination light toward an object, an image acquisition unit acquiring a color image including at least three or more color components by receiving and imaging reflection light from the object with an image sensor, and an evaluation unit performing evaluation relevant to a target illness of each pixel on the basis of an angle between a line segment connecting a predetermined reference point set in a color plane that is defined by at least two color components of at least three or more color components and a pixel corresponding point in a color plane of each of the pixels configuring the color image that is acquired by the image acquisition unit, and a reference axis having a correlation with the target illness. The reference axis is set to pass through the predetermined reference point. The reference axis is at least one of an axis having a correlation with the target illness in which the degree of inflammation in the color plane is less than or equal to a predetermined value and an axis having a correlation with the target illness in which the degree of inflammation is greater than or equal to the predetermined value.

According to such a configuration, a stable inflammation evaluation value can be calculated by suppressing a variation in an inflammation evaluation value due to the brightness of the image, and a processing load for calculating the inflammation evaluation value can be suppressed.

However, the endoscope system may evaluate the inflamed site by using an image including a portion in Which a blood vessel appears in a biological tissue surface. In this case, it is difficult to discriminate the inflamed site and a blood vessel region by the color component, and thus, the inflamed site is evaluated by including the blood vessel region. In this case, the inflammation evaluation value is higher than an evaluation value of only the actual inflamed site, and there is a possibility that the degree of inflammation is not capable of being accurately evaluated. That is, in the endoscope system described above, the degree of inflammation at the inflamed site is not capable of being accurately evaluated in a state where the blood vessel region is removed.

Therefore, an object of the present invention is to provide an endoscope system that is capable of accurately evaluating the degree of inflammation of an inflamed site of a biological tissue.

Solution to Problem

One embodiment of the present invention is an endoscope system. The endoscope system, includes:

an electronic endoscope configured to image a biological tissue in a body cavity;

a processor including an image processing unit configured to obtain an inflammation evaluation value in which a degree of inflammation of the biological tissue is digitized on the basis of information of a color component of an image of the biological tissue, from the image that is obtained by the electronic endoscope; and a monitor configured to display the inflammation evaluation value, in which the image processing unit includes a blood vessel region determination unit configured to obtain certainty of a blood vessel region of the biological tissue in the image, which is digitized, on the basis of a shape featuring a blood vessel, and an evaluation value calculation unit including a pixel evaluation value generation unit configured to obtain a pixel evaluation value by performing digitization processing for digitizing a degree of feature indicated by the inflammation on the basis of information of a color component of each pixel of the image, with respect to each of the pixels of the image, a pixel evaluation value adjustment unit configured to perform correction processing for greatly reducing the pixel evaluation value as the certainty of the blood vessel region is high, with respect to each of the pixels of the image, and an integration unit configured to calculate the inflammation evaluation value by integrating the pixel evaluation values of each of the pixels after the correction processing.

It is preferable that the correction processing is processing for subtracting a value obtained by multiplying a value of the certainty of the blood vessel region by a positive coefficient, from the pixel evaluation value.

It is preferable that the blood vessel region determination unit is configured to obtain the certainty of the blood vessel region by using an image configured of the pixel evaluation value.

Another embodiment of the present invention is an endoscope system. The endoscope system, includes:

an electronic endoscope configured to image a biological tissue in a body cavity;

a processor including an image processing unit configured to obtain an inflammation evaluation value in which a degree of inflammation of the biological tissue is digitized on the basis of information of a color component of an image of the biological tissue, from the image that is obtained by the electronic endoscope; and a monitor configured to display the inflammation evaluation value, in which the image processing unit includes a blood vessel region determination unit configured to extract a blood vessel region h obtaining certainty of the blood vessel region of the biological tissue in the image, which is digitized, on the basis of a shape featuring a blood vessel, and a pixel evaluation value generation unit configured to obtain a pixel evaluation value by performing digitization processing for digitizing a degree of feature indicated by the inflammation on the basis of information of a color component of each pixel of the image, with respect to each of the pixels of the image, a pixel evaluation value adjustment unit configured to perform correction processing for forcibly changing a pixel evaluation value in the extracted blood vessel region in the image to zero and for maintaining a pixel evaluation value in a non-blood vessel region other than the blood vessel region, and an integration unit configured to calculate the inflammation evaluation value by integrating the pixel evaluation values of each of the pixels after the correction processing.

Another embodiment of the present invention is an endoscope system. The endoscope system, includes:

an electronic endoscope configured to image a biological tissue in a body cavity;

a processor including an image processing unit configured to obtain an inflammation evaluation value in which a degree of inflammation of the biological tissue is digitized on the basis of information of a color component of an image of the biological tissue, from the image that is obtained by the electronic endoscope; and a monitor configured to display the inflammation evaluation value, in which the image processing unit includes a blood vessel region determination unit configured to extract a blood vessel region by obtaining certainty of the blood vessel region of the biological tissue in the image, which is digitized, on the basis of a shape featuring a blood vessel, and an evaluation value calculation unit including a pixel evaluation value generation unit configured to obtain a pixel evaluation value by performing digitization processing for digitizing a degree of feature indicated by the inflammation on the basis of information of a color component of each pixel in a non-blood vessel region other than the blood vessel region in the image, with respect to each of the pixels, and an integration unit configured to calculate the inflammation evaluation value by integrating the pixel evaluation values in the non-blood vessel region.

It is preferable that the blood vessel region determination unit includes a plurality of templates having a plurality of linear shapes in which extension directions of straight lines are different from each other, as the shape featuring the blood vessel, and the blood vessel region determination unit is configured to obtain a matching degree representing a degree of correlation between a shape of an examination target area of the image and each of the linear shapes of the plurality of templates and to determine whether or not it is the blood vessel region by a maximum matching degree that is highest in the matching degrees respectively corresponding to the plurality of templates.

It is preferable that the blood vessel region determination unit includes a plurality of templates having a plurality of linear shapes in which extension directions of straight lines are different from each other, as the shape featuring the blood vessel, and the blood vessel region determination unit is configured to obtain a matching degree representing a degree of correlation between a shape of an examination target area of the image and each of the linear shapes of the plurality of templates and to use the highest matching degree in the matching degrees respectively corresponding to the plurality of templates, as the certainty of the blood vessel region in the examination target area.

It is preferable that each of the templates is configured of pixels having a predetermined size and a rectangular shape, and each of the pixels of each of the templates is a space filter having a pixel value set in conformance to the shape, and the blood vessel region determination unit is configured to associate a pixel in the examination target area of the image with each pixel of the space filter and to obtain the matching degree on the basis of a value in which a pixel value of the pixel in the examination target area of the image and a pixel value of a corresponding pixel of the space filter are multiplied and added up.

It is preferable that the evaluation value generation unit is configured to perform the digitization processing with respect to each of the pixels of the image of the biological tissue and to prepare a color map image to which a color is applied in accordance with the pixel evaluation value obtained by the digitization processing, the blood vessel region determination unit is configured to extract the blood vessel region by obtaining the certainty of the blood vessel region with a space filter having a pixel value corresponding to a linear shape, with respect to the image configured of an image evaluation value, and the integration unit is further configured to prepare a blood vessel removal color map image by using an image in which the blood vessel region is removed from the image configured of the pixel evaluation value and to transmit the blood vessel removal map image along with the inflammation evaluation value to be displayed on the monitor.

It is preferable that the color component of the image includes a red component, a green component, and a blue component, and the evaluation value calculation unit is configured to calculate the pixel evaluation value on the basis of a deviation angle deviating with respect to a reference axis set in advance, in which in a color space that is defined by the red component, the blue component, or the green component, a direction of a line segment connecting a reference point set in the color space and a pixel corresponding point corresponding to the color component of each of the pixels of the image passes through the reference point.

Advantageous Effects of Invention

According to the endoscope system described above, it is possible to accurately evaluate the degree of inflammation of an inflamed site of a biological tissue.

DESCRIPTION OF EMBODIMENTS

Figure 1:
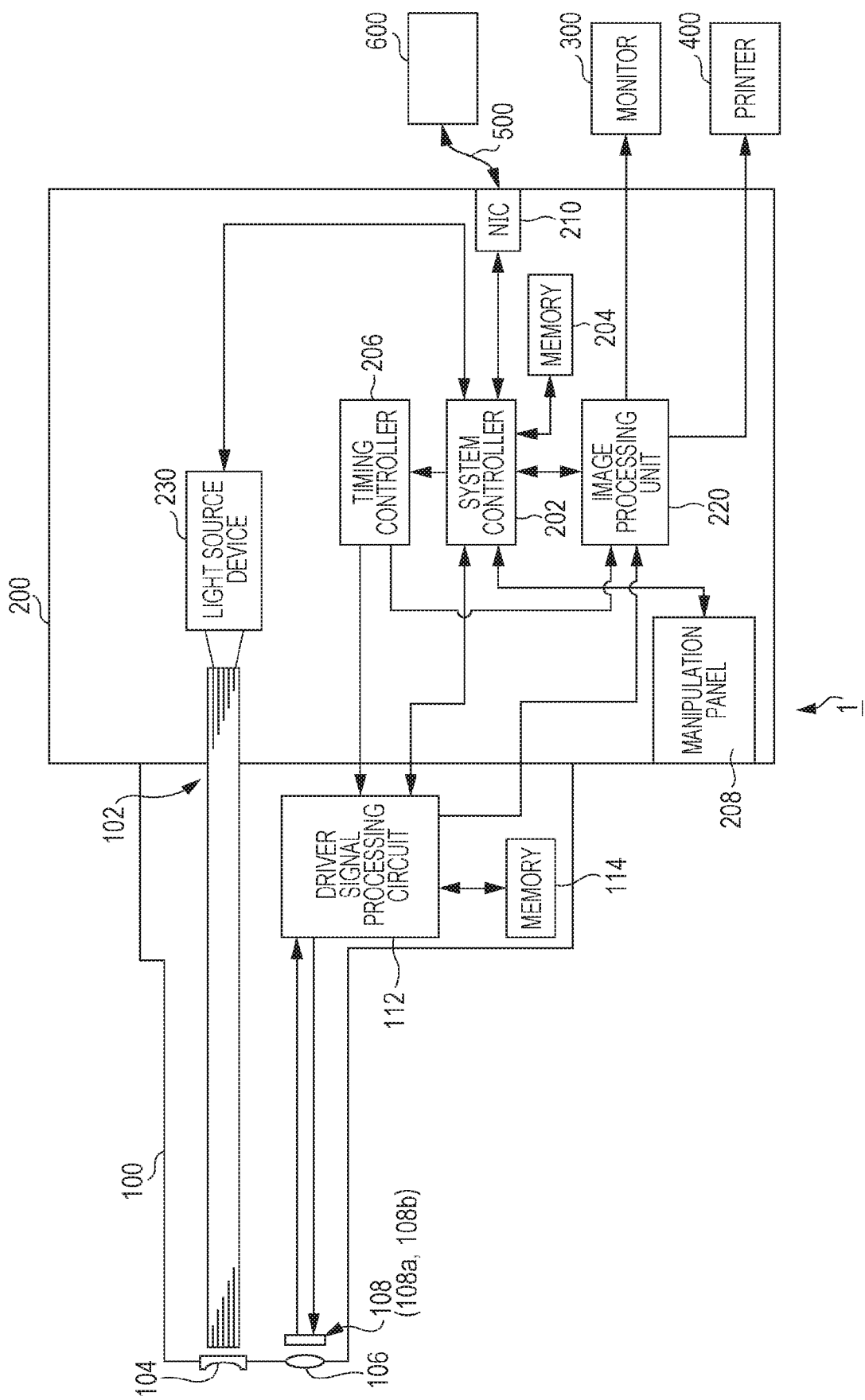
FIG. 1 is a block diagram illustrating a configuration of an endoscope system according to an embodiment.

Hereinafter, an endoscope system of an embodiment will be described with reference to the drawings.

An inflamed site in a biological tissue exhibits a red color, and the degree of inflammation increases as the red color is intensified, and thus, an endoscope system of the related art discriminates the inflamed site and a normal site by using the red color, digitizes the degree of inflammation of the biological tissue on the basis of a color component of each pixel of a photographed image, and calculates an inflammation evaluation value. However, in the biological tissue, in a case where a blood vessel is in the vicinity of a mucosal membrane but not a surface, the blood vessel is visible through the mucosal membrane, and such a portion exhibits the same red color. In a case where pixels of such a portion in which the blood vessel is visible are digitized by the color component, the portion of the blood vessel is erroneously evaluated as an inflammation portion, and thus, the inflammation evaluation value to be calculated is not correct, and has a low accuracy. In order to solve such a problem, an endoscope system of one embodiment determines the certainty of a blood vessel region of a digitized biological tissue in an image obtained by imaging a biological tissue, on the basis of a shape featuring a blood vessel. Further, the endoscope system obtains a pixel evaluation value by performing digitization processing for digitizing the degree of feature indicated by an inflammation, with respect to each of the pixels of the image, on the basis of information of a color component of each of the pixels, and performs correction processing for greatly reducing the obtained pixel evaluation value as the certainty of the blood vessel region is high, with respect to each of the pixels in the region of the image. The pixel evaluation values of each of the pixels after the correction processing will be referred to as an adjustment value. The inflammation evaluation value is calculated by integrating the adjustment values of each of the pixels, obtained as described above.

Alternatively, an endoscope system of another embodiment extracts the blood vessel region by obtaining the certainty of the blood vessel region of the biological tissue in the image that is obtained by imaging the biological tissue, on the basis of the shape featuring the blood vessel. Further, the endoscope system obtains the pixel evaluation value by performing the digitization processing with respect to each of the pixels of the image, on the basis of the information of the color component of each of the pixels, and performs correction processing for forcibly changing the pixel evaluation value in the extracted blood vessel region in the image to zero and for maintaining a pixel evaluation value in a non-blood vessel region other than the blood vessel region. The inflammation evaluation value is calculated by integrating the pixel evaluation values of each of the pixels after the correction processing.

Alternatively, an endoscope system of another embodiment extracts the blood vessel region by obtaining the certainty of the blood vessel region of the biological tissue from a pixel value of a certain color component of the photographed image, on the basis of the shape featuring the blood vessel, and calculates the pixel evaluation value by performing the digitization processing with respect to each of the pixels in the non-blood vessel region other than the blood vessel region in the image, on the basis of the information of the color component of each of the pixels. The inflammation evaluation value is calculated by integrating the calculated pixel evaluation values.

As described above, in any embodiment, the blood vessel region that is discriminated from the inflamed site can be excluded or can be subjected to the correction processing to be excluded from an inflammation evaluation target, at the time of obtaining the inflammation evaluation value, and thus, it is possible to accurately evaluate the degree of inflammation of the inflamed site of the biological tissue.

FIG. 1 is a block diagram illustrating the configuration of an electronic endoscope system 1 of one embodiment.

As illustrated in FIG. 1, the electronic endoscope system 1 includes an electronic scope 100, a processor 200 for an electronic endoscope, a monitor 300, and a printer 400.

The processor 200 for an electronic endoscope includes a system controller 202 and a timing controller 206. The system controller 202 executes various programs stored in a memory 204, and controls integrally the entire electronic endoscope system 1. In addition, the system controller 202 changes various settings of the electronic endoscope system 1 in accordance with an instruction of a user (an operator or an assistant) that is input into a manipulation panel 208. The timing controller 206 outputs a clock pulse for adjusting a performance timing of each unit to each circuit in the electronic endoscope system 1.

The processor 200 for an electronic endoscope includes a light source unit 230 supplying illumination light to the electronic scope 100. Even though it is not illustrated, the light source unit 230, for example, includes a high-luminance lamp emitting white illumination light by receiving the supply of driving power from a lamp power source, for example, a xenon lamp, a metal halide lamp, a mercury lamp, or a halogen lamp. The light source unit 230 is configured such that the illumination light exiting from the high-luminance lamp is condensed by a light condensing lens that is not illustrated, and then, is incident on an incident end of a light carrying bundle (LCB) 102 that is a bundle of optical fibers of the electronic scope 100 through a light control device that is not illustrated.

Alternatively, the light source unit 230 includes a plurality of light emitting diodes allowing light in a wavelength band of a predetermined color to exit. The light source unit 230 is configured such that the light exiting from the light emitting diode is synthesized by using an optical element such as dichroic mirror, and the synthesized light is condensed by the light condensing lens that is not illustrated, as the illumination light, and then, is incident on the incident end of the light carrying bundle (LCB) 102 of the electronic scope 100. A laser diode can also be used instead of the light emitting diode. The light emitting diode and the laser diode have features such as low power consumption and a small heat release value, and thus, there is an advantage that it is possible to acquire a bright image while suppressing the power consumption and the heat release value, compared to other light sources. A bright image can be acquired, and thus, the accuracy of an evaluation value relevant to the inflammation described below can be improved.

Note that, in the example illustrated in FIG. 1, the light source unit 230 is provided by being embedded in the processor 200 for an electronic endoscope, but may be provided in the electronic endoscope system 1, as a device separate from the processor 200 for an electronic endoscope. In addition, the light source unit 230 may be provided on the distal tip of the electronic scope 100 described below. In this case, the LCB 102 guiding the illumination light is not necessary.

The illumination light incident into the LCB 102 from the incident end propagates through the LCB 102 and exits from the exiting end of the LCB 102 that is disposed on the distal tip of the electronic scope 100, and is applied to an object through a light distribution lens 104. Reflection light from the object forms an optical image on a light receiving surface of a solid image sensor 108 through an objective lens 106.

The solid image sensor 108, for example, is a single-plate type color charge-coupled device (CCD) image sensor in which various filters such as infra red (IR) cut filter 108a and a Bayer array color filter 108b are disposed on the light receiving surface, and generates each primary color signal of red (R), green (G), and blue (B) according to the optical image formed on the light receiving surface. A single-plate type color complementary metal oxide semiconductor (CMOS) image sensor can also be used instead of the single-plate type color CCD image sensor. In general, in the CMOS image sensor, an image tends to be generally dark, compared to the CCD image sensor. Accordingly, an advantageous effect that it is possible to suppress a variation in the inflammation evaluation value due to the brightness of the image, in digitization processing for evaluating the degree of inflammation described below, is remarkable compared to the case of using the CMOS image sensor.

A driver signal processing circuit 112 is provided in a connector unit of the electronic scope 100 that is connected to the processor 200 for an electronic endoscope. The driver signal processing circuit 112 generates an image signal (a luminance signal Y and a color difference signals Cb and Cr) by performing predetermined signal processing such as color interpolation and matrix calculation with respect to the primary color signal that is input by the solid image sensor 108, and outputs the generated image signal to an image processing unit 220 of the processor 200 for an electronic endoscope. In addition, the driver signal processing circuit 112 accesses a memory 114, and reads out intrinsic information of the electronic scope 100. The intrinsic information of the electronic scope 100 that is recorded in the memory 114, for example, includes the number of pixels or sensitivity, a performable frame rate, a model number, and the like of the solid image sensor 108. The driver signal processing circuit 112 outputs the intrinsic information that is read out from the memory 114 to the system controller 202. As described above, the electronic scope 100 images the biological tissue in a body cavity by using the solid image sensor 108.

The system controller 202 performs various calculations on the basis of the intrinsic information of the electronic scope 100, and generates a control signal. The system controller 202 controls the performance or the timing of each of the circuits in the processor 200 for an electronic endoscope by using the generated control signal such that processing suitable for the electronic scope 100 being connected to the processor 200 for an electronic endoscope is performed.

The timing controller 206 supplies the clock pulse to the driver signal processing circuit 112, the image processing unit 220, and the light source unit 230, in accordance with timing control of the system controller 202. The driver signal processing circuit 112 drives and controls the solid image sensor 108 at a timing synchronized with a frame rate of a video that is processed on the processor 200 for an electronic endoscope side, in accordance with the clock pulse that is supplied from the timing controller 206.

The image processing unit 220 generates a video signal for displaying an endoscope image or the like on the monitor, on the basis of the image signal input by the driver signal processing circuit 112, and outputs the video signal to the monitor 300, under the control of the system controller 202. Further, the image processing unit 220 performs the digitization processing described below with respect to the image of the biological tissue that is obtained by the electronic scope 100, obtains the inflammation evaluation value indicating the degree of inflammation of the biological tissue that is digitized on the basis of the information of the color component of the image, and generates a color map image in which the pixel evaluation values of each of the pixels that are obtained by the digitization processing are replaced with colors. Specifically, the image processing unit 220 generates a video signal for displaying information of the inflammation evaluation value and the color map image on the monitor, and Outputs the video signal to the monitor 300. Accordingly, the operator is capable of accurately evaluating, for example, the degree of inflammation of an attention biological tissue through the image that is displayed on a display screen of the monitor 300. The image processing unit 220, as necessary, outputs the inflammation evaluation value and the color map image to the printer 400.

The processor 200 for an electronic endoscope is connected to a server 600 through a network interface card (NIC) 210 and a network 500. The processor 200 for an electronic endoscope is capable of downloading information relevant to an endoscopic examination (for example, electronic chart information of a patient or information of an operator) from the server 600. The downloaded information, for example, is displayed on the display screen of the monitor 300 or the manipulation panel 208. In addition, the processor 200 for an electronic endoscope uploads an endoscopic examination result (endoscope image data, an examination condition, an image analysis result, operator findings, and the like) to the server 600, and thus, is capable of storing the endoscopic examination result in the server 600.

Figure 2:
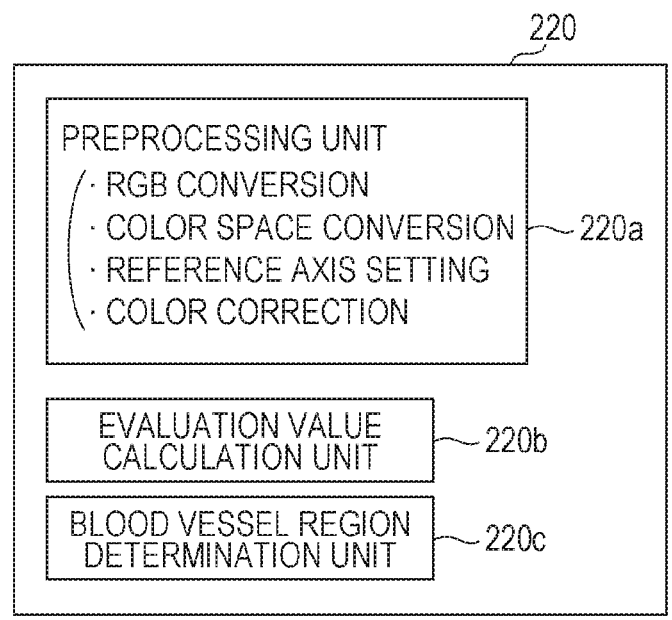
FIGS. 2(a) and 2(b) are diagrams describing a configuration of an image processing unit of one embodiment, which performs digitization processing with respect to an inflammation.
Figure 2:
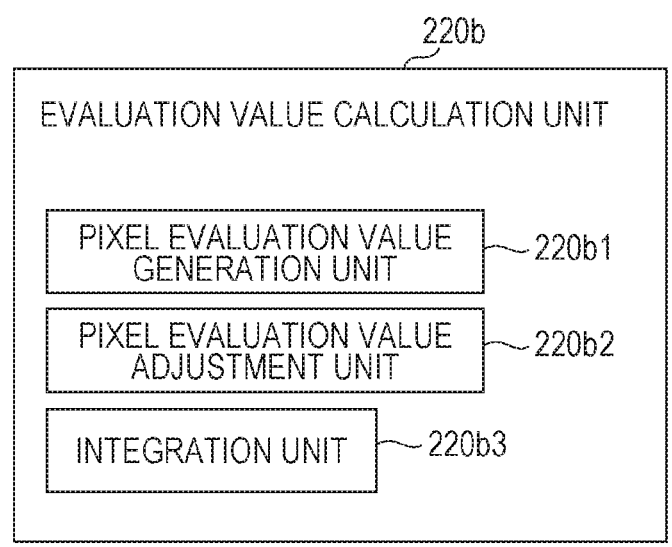

FIGS. 2(*a*) and 2(*b*) are diagrams describing the configuration of the image processing unit 220 performing the digitization processing for digitizing the degree of feature indicated by the inflammation, for each of the pixels, in order to calculate the inflammation evaluation value. The image processing unit 220 calculates the inflammation evaluation value in which the degree of inflammation of the biological tissue is digitized on the basis of the information of the color component of the image, from the image of the biological tissue that is obtained by the electronic scope 100. The image processing unit 220 includes a preprocessing unit 220*a*, an evaluation value calculation unit 220*b*, and a blood vessel region determination unit 220*c*. The evaluation value calculation unit 220*b* includes a pixel evaluation value generation unit 220*b*1, a pixel evaluation value adjustment unit 220*b*2, and an integration unit 220*b*3.

The preprocessing unit 220*a* performs each processing of RGB conversion, color space conversion, reference axis setting, and color correction.

The preprocessing unit 220*a* converts the image signal that is input by the driver signal processing circuit 112 (the luminance signal Y and the color difference signals Cb and Cr) into an age color component (R, G, and B) by using a predetermined matrix coefficient.

Further, the preprocessing unit 220*a* performs color space conversion for orthogonally projecting image data that is converted into the image color component onto an RG plane. Specifically, image color components of each pixel of an RGB color space that is defined by three primary colors of RGB are converted into image color components of RG, Conceptually, the image color components of each of the pixels of the RGB color space are plotted in the RG plane (for example, a section in the RG plane in which Pixel Value of R Component=0 to 255 and Pixel Value of G Component=0 to 255 are obtained), in accordance with the pixel values of the R and G components. Hereinafter, for the convenience of description, points of the image color components of each of the pixels of the RGB color space and points of the image color components that are plotted in the RG color space will be referred to as a "pixel corresponding point". The image color components of each of RGB of the RGB color space, for example, are sequentially a color component having a wavelength of 620 nm to 750 nm, a color component having a wavelength of 495 nm to 570 nm, and a color component having a wavelength of 450 nm to 495 nm. Note that, the color components configure the color space (also including the color plane). A color phase and a chromaticness are excluded from the "color component".

The preprocessing unit 220*a* sets a reference axis in the RG plane that is necessary for evaluating the degree of inflammation in the inflamed site.

In the biological tissue of the body cavity of the patient, which is the object, the R component of the image color components is dominant over the other components (the G component and the B component) by the influence of a hemoglobin pigment or the like, and typically, the red color (the R component) is intensified with respect to other colors (the G component and the B component) as the inflammation becomes severe. However, the color of the image obtained by imaging the body cavity is changed in accordance with a photographing condition affecting the brightness (for example, an exposing condition of the illumination light). Illustratively, a shaded portion that is not exposed to the illumination light is black (an achromatic color, for example, the values of the image color component of R, G, and B are zero or a value close to zero), and a portion that is strongly exposed to the illumination light and is subjected to normal reflection is white (an achromatic color, for example, the values of the image color components of R, G, and B are 255 or a value close to 255 in the case of an 8-bit shade). That is, even in the case of imaging the same inflamed site in which the inflammation occurs, a pixel value of the inflamed site increases as being strongly exposed to the illumination light. For this reason, the value of the color component of the image may have no correlation with the severeness of the inflammation, in accordance with the exposing condition of the illumination light.

In general, a normal site in the body cavity in which the inflammation does not occur is covered with a sufficient mucosal membrane. In contrast, the inflamed site in the body cavity in which the inflammation occurs is not covered with a sufficient mucosal membrane. Specifically, the blood vessel expands and the blood and the body fluid are leaked out from the blood vessel, and thus, the mucosal membrane becomes relatively thin, and the color of the blood is likely to be visible. On the other hand, the mucosal membrane basically has a white tone, but is slightly yellow as a color, and the color (the yellow color) on the image is changed in accordance with a contrasting density of the mucosal membrane (the thickness of the mucosal membrane). Accordingly, it is considered that the contrasting density of the mucosal membrane is also one of the indices for evaluating the severeness of inflammation.

Figure 3:
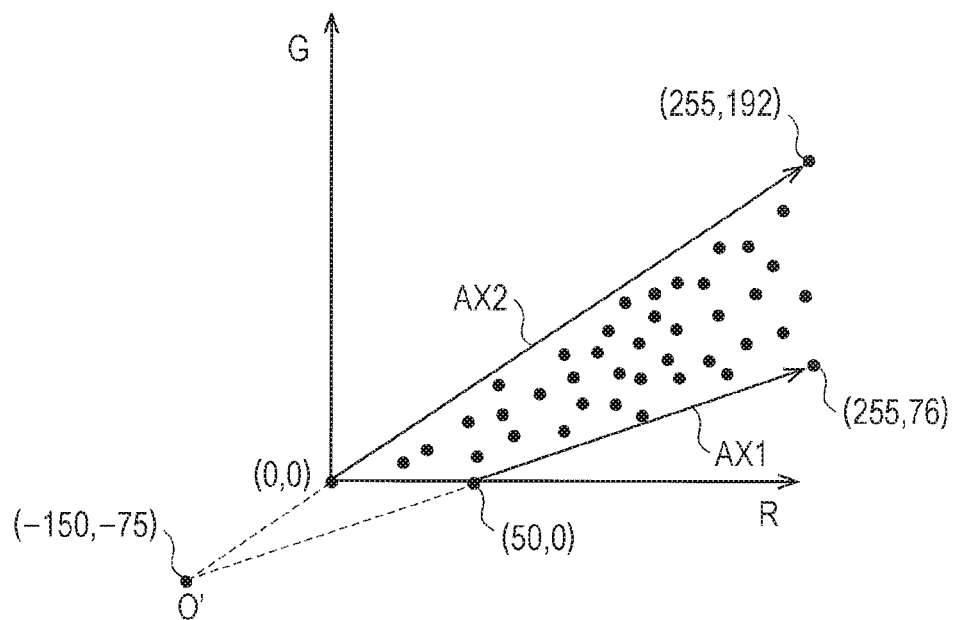
FIG. 3 is a diagram describing an example of a reference axis in a color space, which is used in one embodiment.

Therefore, as illustrated in FIG. 3, in the RG color space, a straight line passing through (50,0) and (255,76) is set as one of the reference axes, and a straight line passing through (0,0) and (255,192) is set as one of the reference axes. For the convenience of description, the reference axis of the former will be referred to as a "hemoglobin change axis AX1", and the reference axis of the latter will be referred to as a "mucosal membrane change axis AX2". FIG. 3 is a diagram describing an example of the reference axis in the color space, which is used in one embodiment.

Plots illustrated in FIG. 3 are obtained as the result of analyzing a plurality of reference images in the body cavity. The reference image used in the analysis includes an inflammation image example at each degree such as an inflammation image example in which the degree of inflammation is highest (an inflammation image example of the most severe level) or an inflammation image example in which the degree of inflammation is lowest (an image example that is substantially regarded as the normal site). Note that, in the example illustrated in FIG. 3, for the convenience of clarifying the drawings, only a part of the plots that are obtained as the result of the analysis is illustrated. The number of plots that are actually obtained as the result of the analysis is considerably greater than the number of plots illustrated in FIG. 3.

As described above, the R component of the color components of the image is intensified with respect to the other components (the G component and the B component) as the inflammation becomes severe. For this reason, an axis on a boundary line between a region in which the plots are distributed and a region in which the plots are not distributed, which is closer to an R axis than a G axis, in the example illustrated in FIG. 3, an axis on a boundary line passing through (50,0) and (255,76) is set as an axis having a high correlation with a portion in which the degree of inflammation is most intensified, that is, a site in which the degree of inflammation is highest. The axis is the hemoglobin change axis AX1. A plot corresponding to an inflamed site in which the degree of inflammation is highest, imaged in various photographing conditions, for example, the exposing condition of the illumination light, is superimposed on the hemoglobin change axis AX1. Therefore, the hemoglobin change axis AX1 is an axis on which the pixel corresponding points to be plotted converge as the degree of inflammation of the biological tissue increases.

On the other hand, the G component (or the B component) of the color components of the image is intensified with respect to the R component as being close to the normal site. For this reason, an axis on the boundary line between the region in which the plots are distributed and the region in which the plots are not distributed, which is closer to the G axis than the R axis, in the example illustrated in FIG. 3, an axis on a boundary line passing through (0,0) and (255,192) is set as an axis having a high correlation with a portion in which the degree of inflammation is lowest, that is, a portion that is substantially regarded as the normal site. The axis is the mucosal membrane change axis AX2. A plot corresponding to the portion in which the degree of inflammation is lowest, that is, the portion that is substantially regarded as a normal portion, imaged in various photographing conditions, for example the exposing condition of the illumination light, is superimposed on the mucosal membrane change axis AX2. Therefore, the mucosal membrane change axis AX2 is an axis on which the pixel corresponding points to be plotted converge as the degree of inflammation decreases (as being close to the normal site).

For supplement, the portion in which the degree of lesion of the lesion portion is highest is accompanied by bleeding. On the other hand, the portion in which the degree of lesion is lowest is the normal site that is substantially normal, and thus, is covered with a sufficient mucosal membrane. For this reason, it is possible to grasp that the plots in the RG color space, illustrated in FIG. 3, are distributed in a region between an axis having the highest correlation with the color of the blood (the hemoglobin pigment) and an axis having the highest correlation with the color of the mucosal membrane. For this reason, in the boundary line between the region in which the plots are distributed and the region in which the plots are not distributed, the boundary line close to the R axis (the R component is intensified) corresponds to an axis indicating the inflamed site in which the degree of inflammation is highest (the hemoglobin change axis AX1), and the boundary line close to the G axis (the G component is intensified) corresponds to an axis indicating the inflamed site in which the degree of inflammation is lowest (the mucosal membrane change axis AX2).

The reference axis is set as described above, and then, processing for calculating inflammation evaluation value indicating the degree of inflammation, described below, is performed with respect to the color component of the image that is orthogonally projected. Color correction is performed with respect to the pixel data that is orthogonally projected, before the processing for calculating the inflammation evaluation value.

The reference axis illustrated in FIG. 3 is an example, and the reference axis is different in accordance with the type of illness.

The preprocessing unit 220a performs the color correction with respect to the color component of the image represented by the RG color space, before the calculation of an inflammation evaluation value. A correction matrix coefficient is stored in a memory which is not illustrated. The preprocessing unit 220a performs correction with respect to the pixel data (R and G) that is the pixel corresponding point in the RG color space of each of the pixels, as indicated in the following expression by using the correction matrix coefficient, such that the inflammation evaluation value described below does not vary at the time of imaging the same inflamed site with different electronic endoscope systems (in other words, such that an error between electronic scopes is suppressed).

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: Pixel Data after Correction (R Component)
$G_{new}$: Pixel Data after Correction (G Component)
$M_{00}$ to $M_{11}$: Correction Matrix Coefficient
R: Pixel Data before Correction (R Component)
G: Pixel Data before Correction (G Component)

The above is the preprocessing that is performed by the preprocessing unit 220a.

Figure 4:
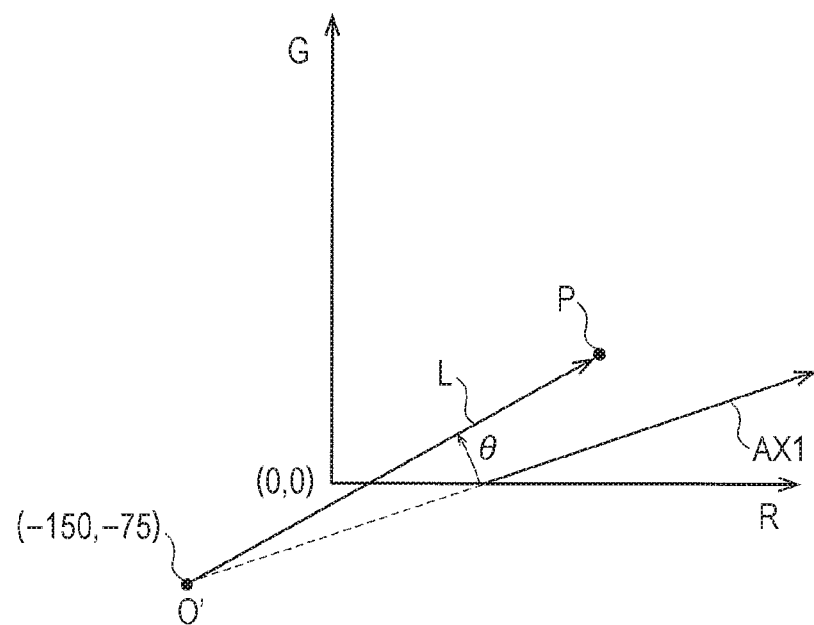
FIG. 4 is a diagram describing an example of a method for calculating a deviation angle for calculating the degree of inflammation, which is used in one embodiment.

The pixel evaluation value generation unit 220b1 of the evaluation value calculation unit 220b selects one attention pixel from the pixels, and calculates a deviation angle for calculating the degree of inflammation on the basis of information of a color component of the attention pixel, with respect to the selected attention pixel, That is, the pixel evaluation value generation unit 220b1 performs the digitization processing for digitizing the degree of feature indicated by the inflammation on the basis of the information of the color component of the pixel. FIG. 4 is a diagram describing an example of a method for calculating the deviation angle for calculating the degree of inflammation, which is used in one embodiment. Specifically, as illustrated in FIG. 4, the pixel evaluation value generation unit 220b1 sets an intersection point between the hemoglobin change axis AX1 and the mucosal membrane change axis AX2 to a reference point O', sets the hemoglobin change axis AX1 as the reference axis, and calculates a deviation angle θ at which the direction of a line segment L connecting the reference point O' and a pixel corresponding point P of the attention pixel with respect to the reference axis. Note that, the reference point O' is positioned at coordinates (−150,−75). An example in which the reference point O' is at the coordinates (−150,−75) is described, but the present invention is not limited thereto. The reference point O' can be suitably changed, and for example, may be an intersection point between the R axis and the G axis in the RG color space.

A preferred coordinate position as the reference point O', for example, is a position in which an error in evaluation results due to a variation in the brightness can be reduced. Specifically, it is preferable to set the reference point O' by obtaining in advance a point at which an error between an evaluation result in a dark portion (a luminance is less than a predetermined value) and an evaluation result in a non-dark portion (the luminance is greater than or equal to the predetermined value) is minimized.

In addition, for example, in a case where the reference point O' is set between coordinates (−10,−10) and coordinates (10,10), a change amount of the angle θ in a case where the pixel corresponding point is changed increases, compared to a case where the coordinates (−150,−75) or the like are set as the reference point O', and thus, resolution is improved. Accordingly, it is possible to obtain an evaluation result having a high accuracy.

On the other hand, the reference point C)' is set between coordinates (−50,−50) and coordinates (−200,−200), and thus, an evaluation result indicating the degree of inflammation is hardly affected by a noise.

In a case where the brightness of the image obtained by photographing the biological tissue in the body cavity is changed in accordance with an exposing condition of white light, the color of the image is affected by an individual difference, a photographing spot, the state of the inflammation, and the like, and in the RG color space, in general, the color of the image is changed along the hemoglobin change axis AX1 in the inflamed site in which the severity is highest, and is changed along the mucosal membrane change axis AX2 in the inflamed site in which the degree of inflammation is lowest. In addition, it is assumed that the color of the image in the inflamed site in which the degree of inflammation is intermediate is changed with the same tendency. That is, in a case where there is a change according to the exposing condition of the illumination light, the pixel corresponding point corresponding to the inflamed site is shifted in an azimuthal direction originating from the reference point O'. In other words, in a case where there is a change according to the exposing condition of the illumination light, the pixel corresponding point corresponding to the inflamed site is moved at a constant deviation angle $\theta$ with respect to the mucosal membrane change axis AX2, and thus, a distance with respect to the reference point O' is changed. This indicates that the deviation angle $\theta$ is a parameter that is not substantially affected by a change in the brightness of the image.

The R component is intensified with respect to the G component as the deviation angle $\theta$ is small, which indicates that the degree of inflammation of the inflamed site is high. In addition, the G component is intensified with respect to the R component as the deviation angle $\theta$ is large, which indicates that the degree of inflamed site is low. Therefore, the evaluation value calculation unit 220b normalizes the angle $\theta$ such that the value is 255 when the deviation angle $\theta$ is zero, and the value is zero when the deviation angle $\theta$ is $\theta_{MAX}$. Note that, $\theta_{MAX}$ is identical to an angle between the hemoglobin change axis AX1 and the mucosal membrane change axis AX2. That is, the evaluation value calculation unit 220b performs the digitization processing for digitizing the degree of feature (the degree of red color) indicated by the inflammation on the basis of the information of the color component of each attention pixel, with respect to each of the attention pixels, and thus, obtains the pixel evaluation value falling within a range of 0 to 255.

Note that, the digitization processing for digitizing the degree of feature (the degree of red color) indicated by the inflammation, which is performed by the pixel evaluation value generation unit 220b1 is performed with respect to the selected attention pixel, and all the pixels of the image can be selected as the attention pixel. In addition, only each pixel of the non-blood vessel region excluding the blood vessel region determined as described below can also be selected. Note that, a case where the pixel evaluation value generation unit 220h1 selects all the pixels without discriminating the blood vessel region and the non-blood vessel region will be described below as an example. Note that, a case where only each of the pixels of the non-blood vessel region is selected, and each of the pixels of the blood vessel region is not selected will be separately described. That is, according to one embodiment, the pixel evaluation value generation unit 220h1 obtains the pixel evaluation value with respect to all pixels of an image of the current frame without discriminating the blood vessel region and the non-blood vessel region.

Note that, in the example illustrated in FIG. 4, the RG color space is used as the color space, but an RB color space can also be used instead of the RG color space.

Further, the pixel evaluation value generation unit 220b1 of the evaluation value calculation unit 220b prepares the color map image in which the image of the biological tissue is formed into a mosaic by a display color that is changed in accordance with the degree of inflammation. In order to enable the color map image to be displayed, a table in which the pixel evaluation value and a predetermined display color are associated with each other is stored in a storage region which is not illustrated. In this table, for example, a different display color is associated at five-value intervals. Illustratively, in a case where the pixel evaluation value is in a range of 0 to 5, a yellow color is associated, a different display color is associated in accordance with an arrangement sequence of colors in a color circle each time when the pixel evaluation value increases by 5, and in a case where the pixel evaluation value is in a range of 250 to 255, a red color is associated. The display color, for example, is a color that becomes closer to a warm color from a cold color as the pixel evaluation value is large. The pixel evaluation value generation unit 220b1 determines the display color of the selected attention pixel on the color map image in accordance with the pixel evaluation value of the attention pixel, on the basis of the table.

As described above, the pixel evaluation value generation unit 220b1 prepares the color map image to which a color is applied in accordance with the pixel evaluation value.

The blood vessel region determination unit 220c determines the certainty of the blood vessel region of the biological tissue in the image that is obtained by imaging the biological tissue, on the basis of the shape featuring the blood vessel, and as necessary, extracts the blood vessel region in accordance with the obtained certainty.

Figure 5:
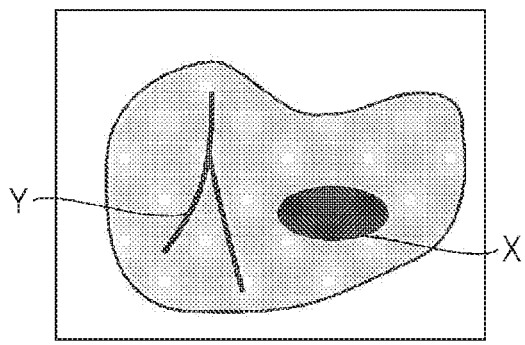
FIGS. 5(a) and 5(b) are diagrams schematically describing an example of an image of a biological tissue and an example of a color map image that is obtained by a method of the related art.
Figure 5:
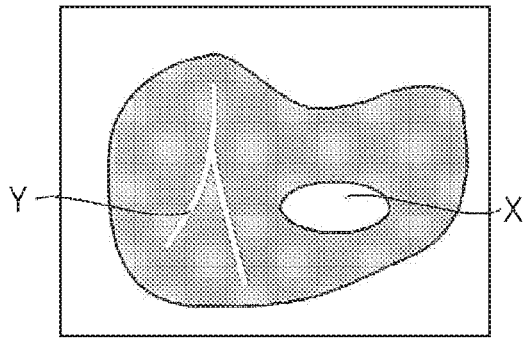

As illustrated in FIG. 5(a), the image obtained by imaging the biological tissue includes an image of a blood vessel region Y in the shape of a streak, which is visible through the mucosal membrane, in addition to an image of an inflamed site X. In a color map image illustrated in FIG. 5(b) in which such an image is color-coded in accordance with the pixel evaluation value described above, the blood vessel region Y may be displayed by the same color as that of the inflamed site. FIGS. 5(a) and 5(b) are diagrams schematically describing an example of the image of the biological tissue and an example of a color map image that is obtained by a method of the related art.

The blood vessel region determination unit 220c obtains the certainty of the blood vessel region Y, and as necessary, extracts the blood vessel region Y.

Figures 6, 7:
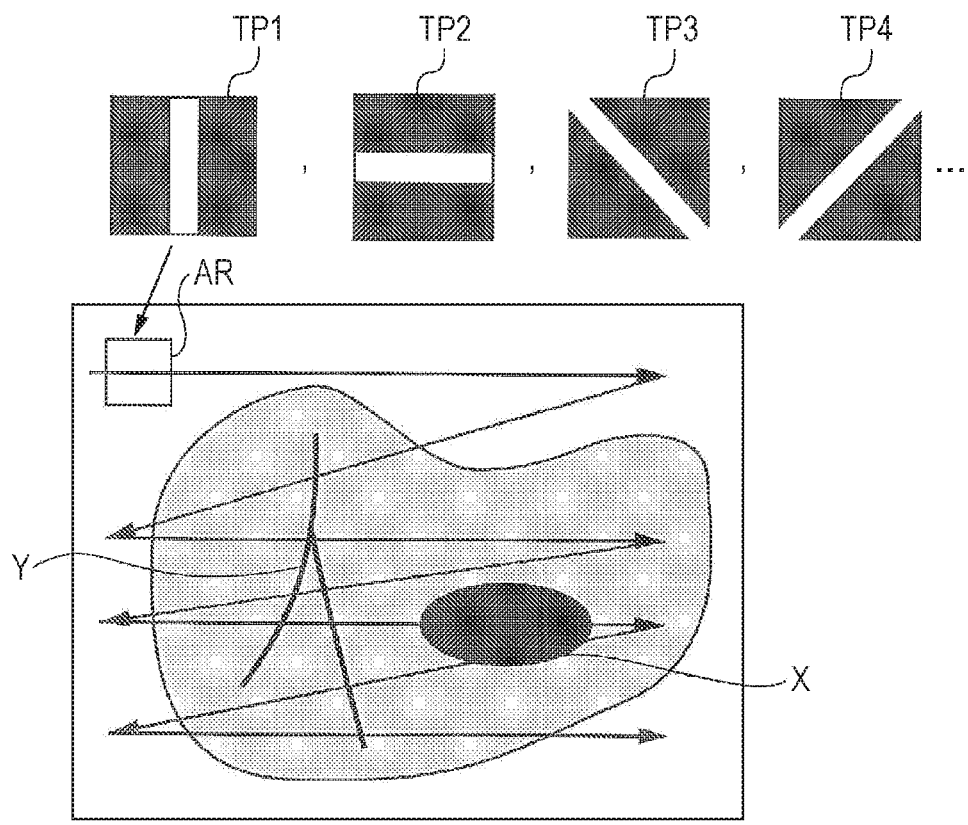
FIG. 6 is a diagram describing an example of a method for extracting a blood vessel region in one embodiment.
FIG. 7 is a diagram illustrating an example of a filter coefficient in the case of using a template TP1 illustrated in FIG. 6 as a space filter.

FIG. 6 is a diagram describing an example of a method for extracting the blood vessel region Y in one embodiment.

The blood vessel region determination unit 220c obtains a matching degree representing the degree of correlation between the shape of a part of an examination target area AR in the image of the biological tissue and each linear shape of a plurality of templates TP1 to TP4, and sets the highest matching degree in the matching degrees respectively corresponding to the plurality of templates TP1 to TP4 as the certainty of the blood vessel region Y in the examination target area AR. The templates TP1 to TP4 are configured of a plurality of pixels, and the templates TP1 to TP4 have a plurality of linear shapes in which extension directions of straight lines are different from each other. In the templates TP1 to TP4, each pixel has a pixel value in conformance to each of the linear shapes. As illustrated in FIG. 6, the examination target area AR is moved while being sequentially overlapped along an arrow from the end of the image, and thus, a correlation degree between the pixel evaluation value of the image in the examination target area AR and the value of the pixel corresponding to each of the templates TN to TP4 is obtained. According to one embodiment, the templates TP1 to TP4 have a plurality of linear shapes in which the straight lines extend in four different extension directions, as the shape featuring the blood vessel. In a case where the examination target area AR includes the blood vessel region Y, the pixel value in the examination target area AR includes information of a feature shape in which the blood vessel extends into the shape of a streak, and thus, the blood vessel region Y can be extracted by using the image described above in which the pixel value is set in accordance e deviation angle θ. The templates TP1 to TP4 have a value for each pixel corresponding to a white region and a black region illustrated in FIG. 6. For this reason, according to one embodiment, the matching degree is a correlation coefficient between the value of the pixel of the templates TP1 to TP4 and the pixel evaluation value corresponding to the examination target region AR.

In addition, according to one embodiment, the matching degree may be a value in which the pixel values of each of the pixels of the templates TP1 to TP4 are set as a filter coefficient of a space filter, and each of the filter coefficients and an image evaluation value of the pixel corresponding to the examination target area AR are multiplied and added up.

The highest matching degree in the matching degrees calculated with respect to each of the templates TP1 to TP4 is set as a value indicating the certainty of the blood vessel region, and is applied to the center pixel of the examination target area AR.

FIG. 7 is a diagram illustrating an example of the filter coefficient in a case where the template TP1 is used as the space filter. As illustrated in FIG. 6, the template TP1 has a shape in which the straight line extends in an up-and-down direction in the drawing. In FIG. 7, as an example, the template TP1 configures a space filter of 5×5 pixels. In this case, ⅕ is applied to pixels of a portion that extends linearly, as the filter coefficient, and −1/20 is applied to the other pixels, as the filter coefficient. When a value in which each filter coefficient and the same image evaluation value of the pixel corresponding to the examination target area AR are multiplied and added up is calculated as the matching degree, the matching degree becomes zero in a case where all of the pixel evaluation values of the examination target area AR are the same value. On the other hand, in a case where the image of the blood vessel extending into the shape of a streak in up-and-down direction is included in the examination target area AR, the matching degree increases. It can be described that an image close to the template TP1 is included as the value of the matching degree is large. Therefore, the matching degree is calculated with respect to each of the templates TP1 to TP4, and the highest matching degree in the calculated matching degrees is set as the certainty of the blood vessel region Y and is applied to the center pixel of the examination target region AR. That is, the value of the certainty of the blood vessel region Y is applied to the center pixel of the examination target area AR.

Such a matching degree is a result of performing space filtering with respect to the pixel evaluation value of the color map image, by using each of the templates TP1 to TP4, and thus, the value of each pixel of an image in which each of the pixels has the pixel evaluation value that is processed by the space filtering includes the shape of the blood vessel region Y matching to any of the templates TP1 to TP4 and the information of the color component, and the image obtained by the space filtering has a pixel value reflecting the blood vessel region Y That is, the pixel value increases as the blood vessel region Y is in the shape of a streak (that is, as the matching degree is high) and the red color included in the blood vessel region is intensified (that is, as the pixel evaluation value is high). Therefore, the blood vessel region determination unit $220c$ generates an image having the value of the certainty of the blood vessel in each of the pixels, obtained as described above, as the pixel value, as the image of the blood vessel region that is extracted on the basis of the pixel evaluation value described above, that is, a blood vessel region image.

The pixel evaluation value adjustment unit $220b2$ adjusts the image evaluation value of each of the pixels that are calculated by the pixel evaluation value generation unit $220b1$. Specifically, the pixel evaluation value adjustment unit $220b2$ performs the correction processing for greatly reducing the pixel evaluation value that is calculated by the pixel evaluation value generation unit $220b1$ as the certainty of the blood vessel region is high, with respect to each of the pixels of the blood vessel region image, and sets the pixel evaluation value after the correction processing as an adjustment value. The pixel evaluation value adjustment unit $220b2$, for example, obtains a value by multiplying the certainty of the blood vessel region of each of the pixels by a coefficient α (α>0) set in advance, and subtracts the value from the pixel evaluation value before the space filtering processing, and thus, obtains the adjustment value.

Therefore, an image having such an adjustment value as the pixel value is an image in which the blood vessel region Y is removed. The pixel evaluation value adjustment unit $220b2$ forms the image into a mosaic by the display color, and thus, prepares a blood vessel removal color map image.

As described above, the pixel evaluation value adjustment unit $220h2$ is capable of obtaining the adjustment value from the pixel evaluation value and the value of the certainty of the blood vessel region Y In an examination target area different from the shape of the templates TP1 to TP4, featuring the blood vessel, for example, the inflamed site X, the degree of certainty of the blood vessel region Y is low, and thus, a change between the pixel evaluation value before the space filtering processing and the adjustment value is small, but in the examination target area AR matching to the shape of the templates TP1 to TP4, the degree of certainty of the blood vessel region is high, and thus, the adjustment value is greatly reduced compared to the pixel evaluation value before the space filtering processing.

The integration unit $220b3$ calculates the inflammation evaluation value by integrating the adjustment values of each of the pixels that are obtained by the pixel evaluation value adjustment unit $220h2$. For example, an average value in which the adjustment values of all the pixels generated by processing the image of the current frame, in images sequentially sent from the electronic scope 100 at a predetermined timing, are averaged is calculated as the inflammation evaluation value of the image. The average value may be a simple average value, or may be a weighted average value. The inflammation evaluation value is not limited to the average value, and may be a value in which the adjustment values of each of the pixels can be integrated into one value. Processing for integrating the adjustment values of each of the pixels into one value may be processing for obtaining, for example, a median value. The processing for integrating the adjustment values of each of the pixels into one value may be processing for calculating a representative value by dividing the adjustment values into at least two or more levels that are ranked and by assigning an addition value P of a value in which the number of pixels belonging to each of the levels is multiplied by a predetermined weighting coefficient to a predetermined expression. In this case, the predetermined expression, for example, is $1/(1+e^{-P})$. In this case, it is preferable that the weighting coefficient is a coefficient that is obtained by multiple logistic regression analysis to have a correlation with the subjective evaluation result of the medical doctor.

The integration unit 220*b*3 sends such an inflammation evaluation value to the monitor 300 to be displayed on the screen along with the blood vessel removal color map image in which the blood vessel region Y is removed.

The inflammation evaluation value may be sent to the monitor 300 to be displayed on the screen along with the color map image before the blood vessel region Y is removed, along with the original color map image. In addition, the inflammation evaluation value may be sent to the monitor 300 to be displayed on the screen along with the image obtained by imaging the current frame input by the driver signal processing circuit 112, along with the image obtained by imaging the current frame.

Figure 8:
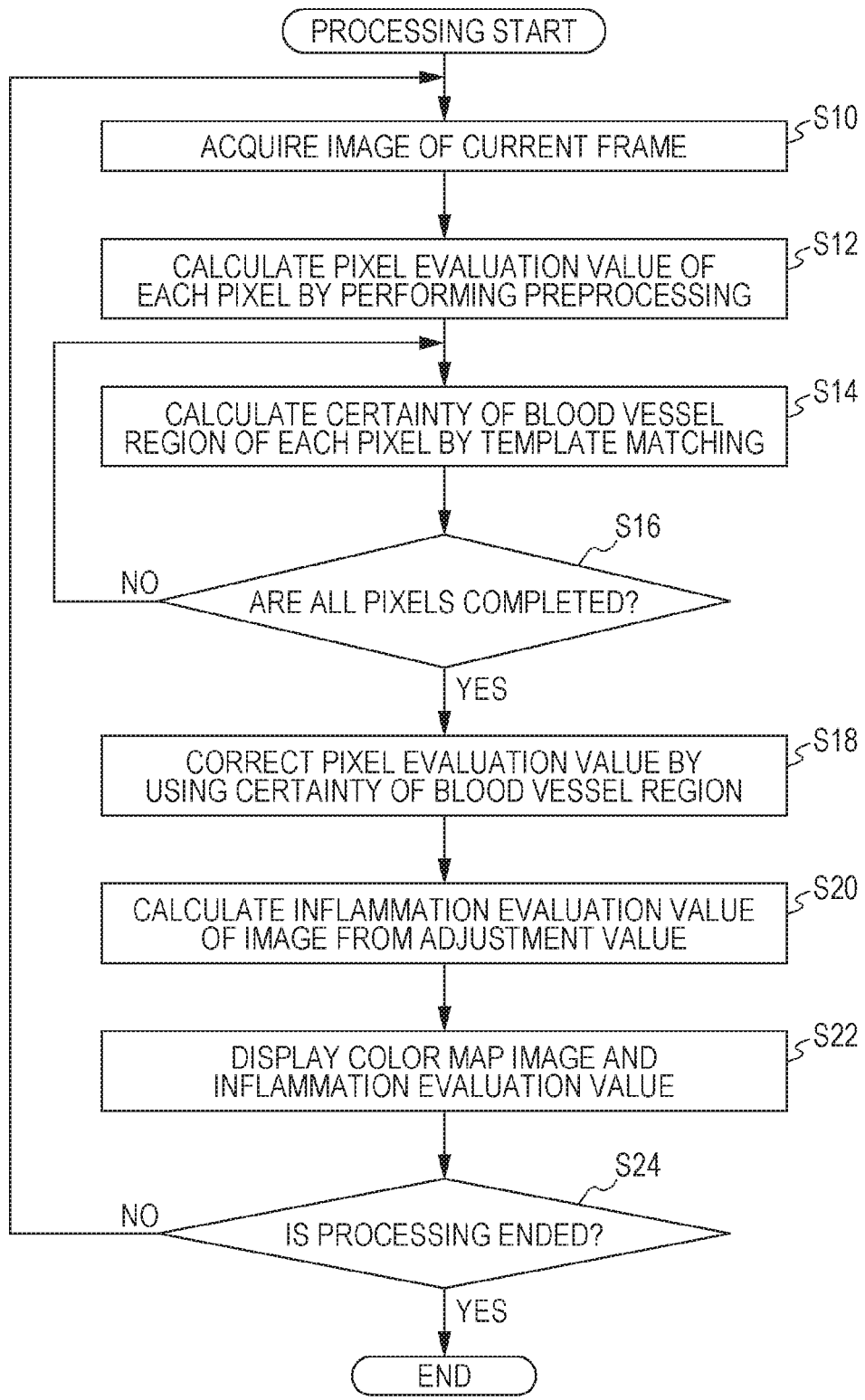
FIG. 8 is a diagram illustrating an example of a flow of processing for calculating an inflammation evaluation value by a processor for an electronic endoscope of one embodiment.

The processor 200 for an electronic endoscope including such an image processing unit 220 calculates the inflammation evaluation value in accordance with a flow illustrated in FIG. 8, and displays the inflammation evaluation value on the monitor 300. FIG. 8 is a diagram illustrating an example of a flow of processing for calculating the inflammation evaluation value by the processor 200 for an electronic endoscope of one embodiment.

First, the image processing unit 220 acquires an image of the current frame (step S10).

Next, the preprocessing unit 220*a* performs preprocessing including the RGB conversion, the color space conversion, the reference axis setting, and the color correction, described above, and the pixel evaluation value generation unit 220*b*1 calculates the pixel evaluation value with respect to the image subjected to the preprocessing, on the basis of the deviation angle θ illustrated in FIG. 4 (step S12).

Next, the blood vessel region determination unit 220*c* performs template matching with respect to an image configured of the calculated pixel evaluation values, by using the templates TP1 to TP4 as illustrated in FIG. 6, and calculates the certainty of the blood vessel region Y of each of the pixels (step S14).

The blood vessel region determination unit 220*c* determines whether or not to calculate the certainty of the blood vessel region Y with respect to all the pixels (step S16). As described above, step S14 is repeated until the certainty of the blood vessel region Y is calculated with respect to all the pixels.

Figure 9:
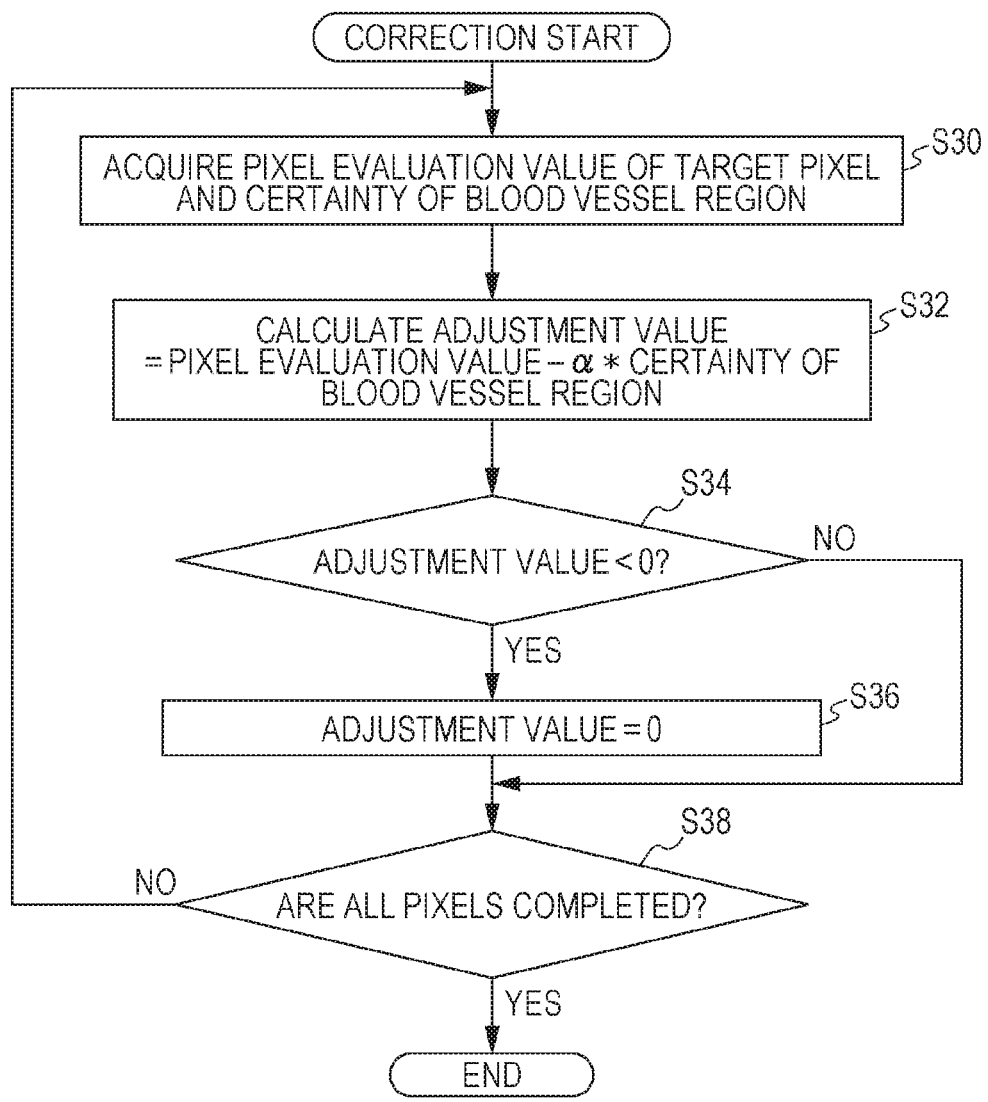
FIG. 9 is a diagram describing an example of a flow of correction processing to be performed with respect to a pixel evaluation value in one embodiment.

Next, the pixel evaluation value adjustment unit 220*b*2 corrects the pixel evaluation value by using the certainty of the blood vessel region Y, and acquires the adjustment value (step S18). FIG. 9 is a diagram describing an example of the flow of correction processing to be performed with respect to the pixel evaluation value.

As illustrated in FIG. 9, in order to correct each of the pixels, the pixel evaluation value adjustment unit 220*b*2 acquires the pixel evaluation value of a target pixel that is calculated by the pixel evaluation value generation unit 220*b*1, and the certainty of the blood vessel region Y that is calculated by the blood vessel region determination unit 220*c* (step S30), Further, the pixel evaluation value adjustment unit 2202 subtracts a result of multiplying the value of the certainty of the blood vessel region Yin the target pixel by the coefficient α set in advance from the pixel evaluation value of the target pixel, and thus, calculates the adjustment value (step S32). The adjustment value in a pixel in which the certainty of the blood vessel region Y is high is a value that is greatly reduced from the pixel evaluation value, and the adjustment value in a pixel in which the certainty of the blood vessel region Y is low has a small reduction amount from the pixel evaluation value.

Further, the pixel evaluation value adjustment unit 220*b*2 determines whether or not the calculated adjustment value is a negative value (step S34). The pixel evaluation value adjustment unit 220*b*2 sets the adjustment value to zero in a case where the adjustment value is a negative value (step S36), and remains the adjustment value in a case where the adjustment value is zero or a positive value.

The pixel evaluation value adjustment unit 220*b*2 determines whether or not all the pixels are subjected to the processing of steps S30 to S36, as the target pixel (step S38). As described above, the pixel evaluation value adjustment unit 220*b*2 corrects the pixel evaluation value by using the certainty of the blood vessel region Y, with respect to all the pixels as the target pixel (step S18).

Next, returning to the flow illustrated in FIG. 8, the integration unit 220*b*3 calculates the inflammation evaluation value from the calculated adjustment value (step S22). For example, an average value in which the adjustment values of all the pixels are averaged is calculated as the inflammation evaluation value.

Further, the integration unit 220*b*3 sends the calculated inflammation evaluation value and the color map image to the monitor 300, and allows the monitor 300 to display the color map image that is prepared at the time of calculating the inflammation evaluation value, and the image evaluation value or the adjustment value (step S22). The color map image may be the original color map image in which the blood vessel region Y is not removed, or may be the blood vessel removal color map image in which the blood vessel region Y is removed. In addition, the image of the current frame may be sent to the monitor 300 along with the inflammation evaluation value, instead of the color map image, and the image of the current frame may be displayed.

As described above, the image processing unit 220 repeats the processing while the photographed image is sequentially sent from the electronic scope 100 (step S24).

As described above, in one embodiment described above, the pixel evaluation value is obtained by performing the digitization processing for digitizing the degree of feature indicated by the inflammation on the basis of the information of the color component of each of the pixels, with respect to each of the pixels of the image, the adjustment value is calculated by performing the correction processing for reducing the obtained pixel evaluation value as the certainty of the blood vessel region Y is high, with respect to each of the pixels of the region of the image, and the inflammation evaluation value is calculated by integrating the calculated adjustment values of each of the pixels. In the embodiment described above, it is possible to perform correction (adjustment) such that the blood vessel region Y that is \discriminated from the inflamed site is excluded from the inflammation evaluation target at the time of obtaining the inflammation evaluation value, and thus, it is possible to accurately evaluate the degree of inflammation of the inflamed site of the biological tissue.

Figure 10:
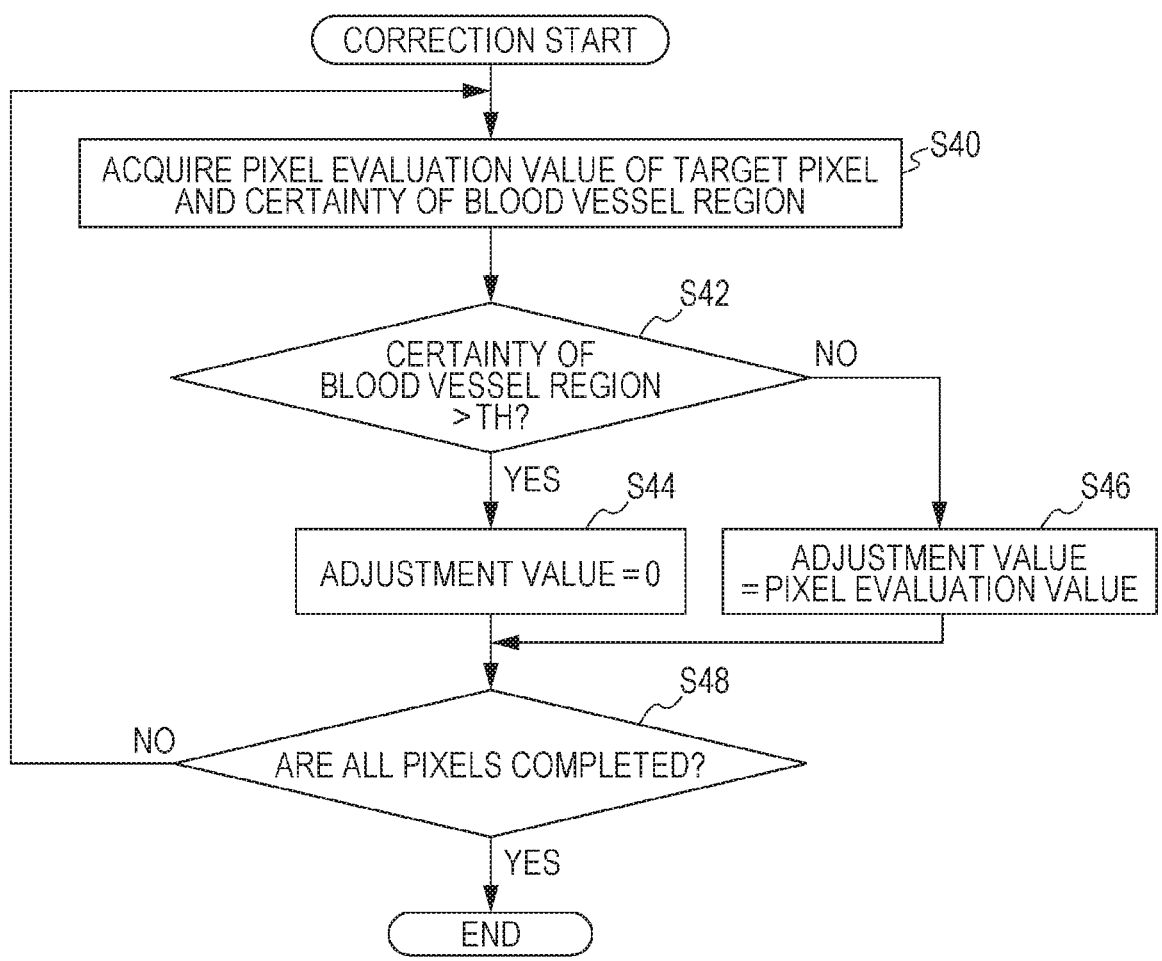
FIG. 10 is a diagram describing an example of a flow of correction processing to be performed with respect to an image evaluation value in one embodiment, which is different from the correction illustrated in FIG. 9.

FIG. 10 is a diagram describing an example of a flow of correction processing to be performed with respect to the image evaluation value in step S18 illustrated in FIG. 8, which is different from the correction processing illustrated in FIG. 9.

In the embodiment illustrated in FIG. 9, the pixel evaluation value generation unit 220*b*1 obtains the pixel evaluation value by performing the digitization processing for digitizing the degree of feature of the color component indicated by the inflammation on the basis of the information of the color component of each of the pixels, with respect to each of the pixels of the image.

The blood vessel region determination unit 220c (refer to FIG. 2(a)) extracts the blood vessel region Y by obtaining the certainty of the blood vessel region Y of the biological tissue in the image, on the basis of the shape featuring the blood vessel. The pixel evaluation value adjustment unit 220b2 performs the correction for forcibly changing the pixel evaluation value in the extracted blood vessel region Y in the image to zero and for maintaining the pixel evaluation value in the non-blood vessel region other than the blood vessel region Y. The integration unit 220b3 calculates the inflammation evaluation value by integrating the pixel evaluation values of each of the pixels after the correction.

As illustrated in FIG. 10, in order to correct the values of each of the pixels, the pixel evaluation value adjustment unit 220b2 acquires the pixel evaluation value of the target pixel that is calculated by the pixel evaluation value generation unit 220b1 and the certainty of the blood vessel region Y that is calculated by the blood vessel region determination unit 220c (step S40).

Further, the pixel evaluation value adjustment unit 220b2 determines whether or not the certainty of the blood vessel region Y is greater than the threshold value TH set in advance (step S42).

In the determination, in a case where the certainty of the blood vessel region Y is greater than the threshold value TH, the pixel is set to the pixel in the blood vessel region Y, the pixel evaluation value is forcibly changed to zero, and the value of zero is set to the adjustment value (step S44). On the other hand, in a case where the certainty of the blood vessel region Y is less than or equal to the threshold value TH, the pixel is set to the pixel in the non-blood vessel region, and the image evaluation value is directly set to the adjustment value (step S46).

The pixel evaluation value adjustment unit 220b2 determines whether or not the adjustment value is acquired with respect to all the pixels (step S48). As described above, the adjustment value is acquired with respect to all the pixels.

The integration unit 220b3 calculates the inflammation evaluation value from the obtained adjustment value. For example, an average value in which the adjustment values of all the pixels are averaged is calculated as the inflammation evaluation value.

As described above, in one embodiment in which the flow illustrated in FIG. 10 is performed, the blood vessel region determination unit 220c extracts the blood vessel region Y by obtaining the certainty of the blood vessel region Y of the biological tissue in the image that is obtained by imaging the biological tissue, on the basis of the shape featuring the blood vessel. The pixel evaluation value generation unit 220b1 obtains the pixel evaluation value by performing the digitization processing for digitizing the degree of feature indicated by the inflammation on the basis of the information of the color component of each of the pixels, with respect to each of the pixels of the image. The pixel evaluation value adjustment unit 220b2 performs the correction for forcibly changing the pixel evaluation value in the extracted blood vessel region Y in the image to zero and for maintaining the pixel evaluation value in the non-blood vessel region. Accordingly, the integration unit 220b3 calculates the inflammation evaluation value by integrating the pixel evaluation values of each of the pixels after the correction. Accordingly, it is possible to exclude the blood vessel region Y that is discriminated from the inflamed site from the inflammation evaluation target at the time of obtaining the inflammation evaluation value, and thus, it is possible to accurately evaluate the degree of inflammation of the inflamed site of the biological tissue.

Figure 11:
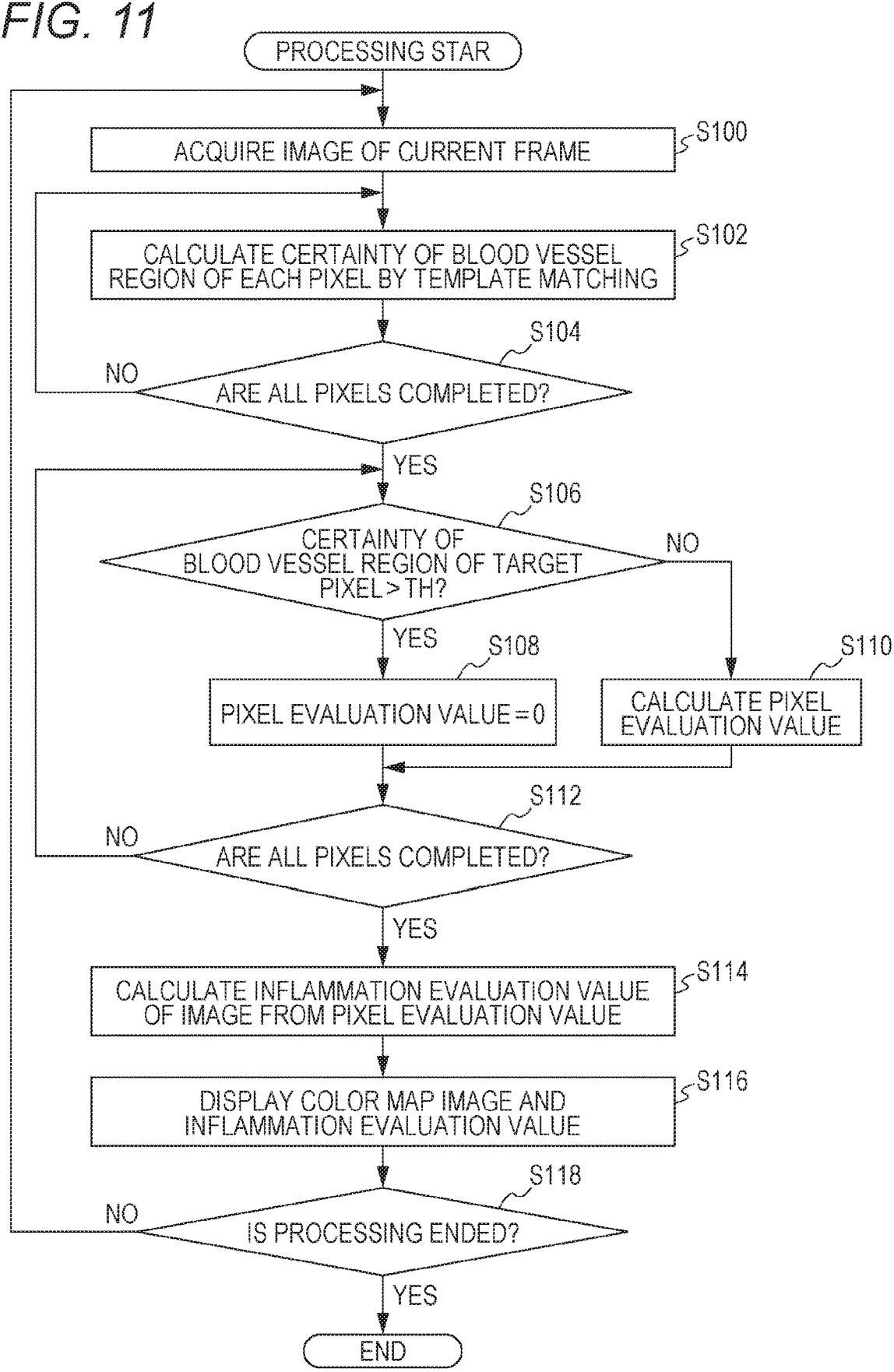
FIG. 11 is a diagram describing an example of a flow of one embodiment, which is different from the flow of calculating the inflammation evaluation value, illustrated in FIG. 8.

In the flow illustrated in FIG. 8, the pixel evaluation value calculated from the deviation angle θ is used as the pixel value of the image for determining the blood vessel region Y but the pixel value of the image for determining the blood vessel region Y may not be necessarily the pixel evaluation value, and for example, may be pixel values of the color components of R, G, B, and the like of the photographed image sent from the electronic scope 100 or pixel values in Y, Cr, and Cb signals. An image value of a certain color component includes a streak shape specific to the blood vessel. For this reason, the pixel value of the image is used, and the certainty of the blood vessel region Y is determined by performing template matching with the templates TP1 to TP4 described above, and the like. FIG. 11 is a diagram describing an example of a flow different from the flow of calculating the inflammation evaluation value, illustrated in FIG. 8.

As illustrated in FIG. 11, the image processing unit 220 acquires the image of the current frame (step S100).

Next, the blood vessel region determination unit 220c calculates the certainty of the blood vessel region Y by performing the template matching using the templates TP1 to TP4 as illustrated in FIG. 6, with respect to each of the pixels of the image of a certain image signal in the image of the current frame (step S102). The blood vessel region determination unit 220c determines whether or not the certainty of the blood vessel region Y is calculated with respect to all the pixels (step S104). As described above, the blood vessel region determination unit 220c repeats step S102 until the certainty of the blood vessel region Y is calculated with respect to all the pixels.

Next, the pixel evaluation value generation unit 220b2 determines whether or not the value of the certainty of the blood vessel region Y of the target pixel is greater than the threshold value TH set in advance (step S106).

In a case where the value of the certainty of the blood vessel region is greater than the threshold value TH set in advance, the pixel evaluation value generation unit 220b1 forcibly sets the pixel evaluation value to zero (step S108). On the other hand, in a case where the value of the certainty of the blood vessel region Y is less than or equal to the threshold value TH set in advance, the pixel evaluation value generation unit 220b1 performs the digitization processing for digitizing the degree of feature indicated by the inflammation on the basis of the information of the color component of each of the pixels, with respect to each of the pixels in the non-blood vessel region other than the blood vessel region. For example, the pixel evaluation value is calculated on the basis of the deviation angle θ illustrated in FIG. 4 (step S110). The pixel evaluation value generation unit 220b1 determines whether or not step S106 and step S108 or step 110 is performed with respect to all the pixels (step S112). As described above, the pixel evaluation value generation 220b1 repeats step S106 and step S108 or step 110 with respect to the target pixel. Accordingly, as described above, the pixel evaluation value generation unit 220b1 prepares the color map image from the obtained pixel evaluation value.

Next, the integration unit 220b3 calculates the inflammation evaluation value from the obtained pixel evaluation value (step S114). For example, the average value in which the pixel evaluation value of all the pixels are averaged is calculated as the inflammation evaluation value.

Further, the integration unit 220b3 sends the calculated inflammation evaluation value and the color map image that is prepared at the time of calculating the pixel evaluation value to the monitor 300, and allows the monitor 300 to display the inflammation evaluation value and the color map image (step S22). The image of the current frame may be displayed on the monitor 300 along with the inflammation evaluation value, instead of the color map image.

As described above, the image processing unit 220 repeats the processing while the photographed image is sequentially sent from the electronic scope 100 (step S118).

As described above, in the flow illustrated in FIG. 11, the blood vessel region determination unit 220c extracts the blood vessel region Y by obtaining the certainty of the blood vessel region Y of the biological tissue from the pixel value of a certain signal of the photographed image but not the pixel evaluation value for preparing the color map image, the pixel evaluation value generation unit 220b1 calculates the pixel evaluation value by performing the digitization processing for digitizing the degree of feature indicated by the inflammation on the basis of the information of the color component of each of the pixels, with respect to each of the pixels in the non-blood vessel region other than the blood vessel region in the image, and the integration unit 220b3 calculates the inflammation evaluation value by integrating the calculated pixel evaluation values. For this reason, it is possible to accurately evaluate the degree of inflammation of the inflamed site of the biological tissue.

As described above, as illustrated in FIG. 6, the blood vessel region determination unit 220c includes the plurality of templates having the plurality of linear shapes in which the straight lines are inclined in a plurality of direction, as the shape featuring the blood vessel, and the blood vessel region determination unit 220c obtains the matching degree representing the degree of correlation between the shape of the examination target area AR of the image and each of the linear shapes of the plurality of templates, and uses the highest matching degree in the matching degrees respectively corresponding to the plurality of templates TP1 to TP4, as the certainty of the blood vessel region Y in the examination target area AR, and thus, is capable of accurately determining the blood vessel region Y even in a case where the blood vessel extends into the shape of a streak towards various directions. In the example illustrated in FIG. 6, the number of templates is four, and five or more templates with various extension directions of the linear shape may be used.

In addition, as with step S42 illustrated in FIG. 10 or step S106 illustrated in FIG. 11, the blood vessel region determination unit 220c obtains the matching degree representing the degree of correlation between the shape of the examination target area AR of the image and each of the linear shapes of the plurality of templates TP1 to TP4, and determines whether or not it is the blood vessel region Y by the highest matching degree in the matching degrees respectively corresponding to the plurality of templates TP1 to TP4, and thus, is capable of efficiently extracting the blood vessel region Y.

According to one embodiment, in a case where each of the templates TP1 to TP4 is configured of pixels having a predetermined size and a rectangular shape and is the space filter configured of the pixel values in which each of the pixels of each of the templates TP1 to TP4 is set in conformance to the linear shape, it is preferable that the blood vessel region determination unit 220c associates the pixel of the examination target area AR of the image with each pixel of the space filter, and obtains the matching degree on the basis of the value in which the pixel value of the pixel of the examination target area AR of the image and the pixel value of the pixel corresponding to the space filter are multiplied and added up. In such processing, calculation can be performed as the space filtering processing, and thus, the template matching can be performed at a high speed.

Figure 12:
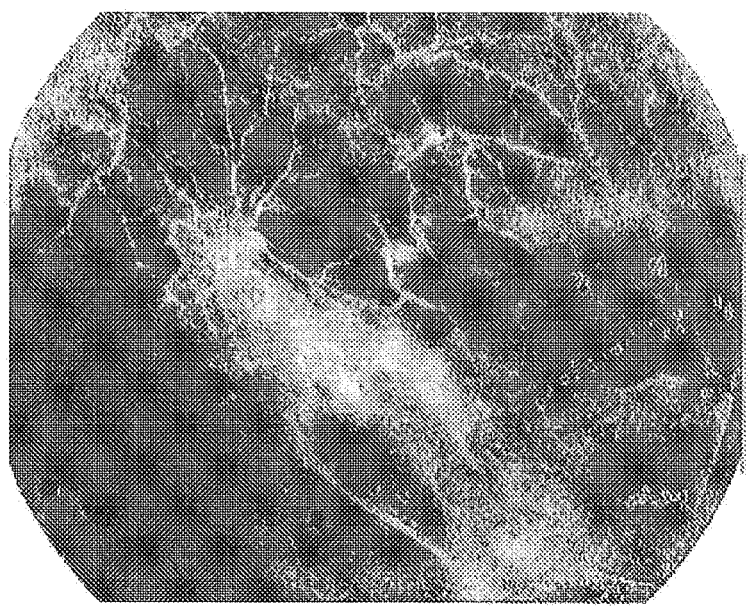
FIG. 12 is a diagram illustrating an example of a color map image including a blood vessel region.
Figure 13:
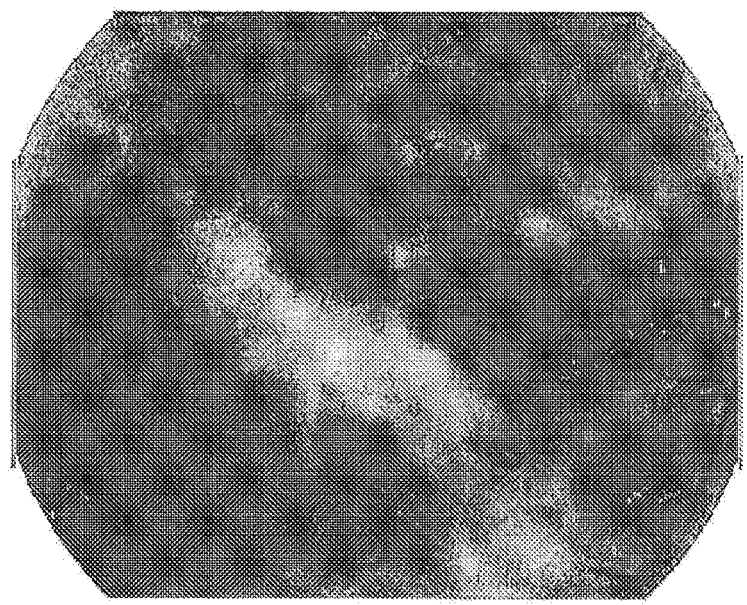
FIG. 13 is a diagram illustrating an example of a blood vessel removal color map image.

In addition, as described above, the blood vessel region determination unit 220c extracts the blood vessel region V by obtaining the certainty of the blood vessel region Y with the space filter having the pixel value corresponding to the linear shape, with respect to the image configured of the image evaluation value. The integration unit 220b3 prepares the blood vessel removal color map image by using the image in which the blood vessel region Y is removed from the image configured of the pixel evaluation value, and transmits the blood vessel removal map image to the monitor 300 along with the inflammation evaluation value to be displayed. Accordingly, the blood vessel removal color map image in which the blood vessel region is removed is displayed on the monitor 300. For this reason, the operator is capable of correctly recognizing the degree of inflammation by observing the blood vessel removal color map image and the inflammation evaluation value. FIG. 12 is a diagram illustrating an example of the color map image including the blood vessel region Y, and FIG. 13 is an example of the blood vessel removal color map image. In FIG. 13, the blood vessel region Y in the shape of a streak as illustrated in FIG. 12 is not seen, and only the inflamed site is displayed.

The color component of the photographed image that is sent from the electronic scope 100 includes the red component, the green component, and the blue component, and as illustrated in FIG. 4, in the color space that is defined by the red component, the blue component, or the green component, the pixel evaluation value generation unit 220b1 calculates the pixel evaluation value on the basis of the deviation angle $\theta$ at which the direction of the line segment L connecting the reference point O' set in the color space and the pixel corresponding point P corresponding to the color component of each pixel of the image deviates with respect to the reference axis such as the hemoglobin change axis AX1, and thus, it is possible to objectively evaluate the degree of inflammation regardless of whether the image is bright or dark.

As described above, the endoscope system has been described in detail, but the endoscope system is not limited to the embodiment described above, and it is obvious that various improvements or modifications may be made within a range not departing from the gist of the present invention.

REFERENCE SIGNS LIST

1 Electronic endoscope system
100 Electronic scope
200 Processor for electronic endoscope
220 Image processing unit
220a Preprocessing unit
220b Evaluation value calculation unit
220b1 Pixel evaluation value generation unit
220b2 Pixel evaluation value adjustment unit
220b3 Integration unit
220c Blood vessel region determination unit
777 Memory
224 Image memory
230 Light source unit
300 Monitor
400 Printer
600 Server

The invention claimed is:

1. An endoscope system, comprising:
   an electronic endoscope configured to image a biological tissue in a body cavity;
   a processor including an image processor configured to obtain an inflammation evaluation value in which a degree of inflammation of the biological tissue is digitized on the basis of information of a color component of an image of the biological tissue, from the image that is obtained by the electronic endoscope;
   a monitor configured to display the inflammation evaluation value; and
   a memory including at least one set of instructions, which when executed by the image processor, causes the image processor to operate as:
      a blood vessel region determination processor configured to obtain certainty of a blood vessel region of the biological tissue in the image, which is digitized, on the basis of a shape featuring a blood vessel, and
      an evaluation value calculation processor including a pixel evaluation value generation processor configured to obtain a pixel evaluation value by performing digitization processing for digitizing a degree of feature indicated by the inflammation on the basis of information of a color component of each pixel of the image, with respect to each of the pixels of the image, a pixel evaluation value adjustment processor configured to perform correction processing for reducing the pixel evaluation value as the certainty of the blood vessel region increases, with respect to each of the pixels of the image, and an integration processor configured to calculate the inflammation evaluation value by integrating the pixel evaluation values of each of the pixels after the correction processing,
      wherein the correction processing comprises subtracting a value obtained by multiplying a value of the certainty of the blood vessel region by a positive coefficient, from the pixel evaluation value.

2. The endoscope system according to claim 1, wherein the blood vessel region determination processor is configured to obtain the certainty of the blood vessel region by using an image composed of the pixel evaluation value.

3. An endoscope system, comprising:
   an electronic endoscope configured to image a biological tissue in a body cavity;
   a processor including an image processor configured to obtain an inflammation evaluation value in which a degree of inflammation of the biological tissue is digitized on the basis of information of a color component of an image of the biological tissue, from the image that is obtained by the electronic endoscope;
   a monitor configured to display the inflammation evaluation value; and
   a memory including at least one set of instructions, which when executed by the image processor, causes the image processor to operate as:
      a blood vessel region determination processor configured to extract a blood vessel region by obtaining certainty of the blood vessel region of the biological tissue in the image, which is digitized, on the basis of a shape featuring a blood vessel, and
      a pixel evaluation value generation processor configured to obtain a pixel evaluation value by performing digitization processing for digitizing a degree of feature indicated by the inflammation on the basis of information of a color component of each pixel of the image, with respect to each of the pixels of the image, a pixel evaluation value adjustment processor configured to perform correction processing for forcibly changing a pixel evaluation value in the extracted blood vessel region in the image to zero and for maintaining a pixel evaluation value in a non-blood vessel region other than the blood vessel region, and an integration processor configured to calculate the inflammation evaluation value by integrating the pixel evaluation values of each of the pixels after the correction processing,
      wherein the correction processing comprises subtracting a value obtained by multiplying a value of the certainty of the blood vessel region by a positive coefficient, from the pixel evaluation value.

4. An endoscope system, comprising:
   an electronic endoscope configured to image a biological tissue in a body cavity;
   a processor including an image processor configured to obtain an inflammation evaluation value in which a degree of inflammation of the biological tissue is digitized on the basis of information of a color component of an image of the biological tissue, from the image that is obtained by the electronic endoscope;
   a monitor configured to display the inflammation evaluation value; and
   a memory including at least one set of instructions, which when executed by the image processor, causes the image processor to operate as:
      a blood vessel region determination processor configured to extract a blood vessel region by obtaining certainty of the blood vessel region of the biological tissue in the image, which is digitized, on the basis of a shape featuring a blood vessel, and
      an evaluation value calculation processor including a pixel evaluation value generation processor configured to obtain a pixel evaluation value by performing digitization processing for digitizing a degree of feature indicated by the inflammation on the basis of information of a color component of each pixel in a non-blood vessel region other than the blood vessel region in the image, with respect to each of the pixels, and an integration processor configured to calculate the inflammation evaluation value by integrating the pixel evaluation values in the non-blood vessel region,
      wherein the correction processing comprises subtracting a value obtained by multiplying a value of the certainty of the blood vessel region by a positive coefficient, from the pixel evaluation value.

5. The endoscope system according to claim 3, wherein the blood vessel region determination processor includes a plurality of templates having a plurality of linear shapes in which extension directions of straight lines are different from each other, as the shape featuring the blood vessel, and
   the blood vessel region determination processor is configured to obtain a matching degree representing a degree of correlation between a shape of an examination target area of the image and each of the linear shapes of the plurality of templates and to determine whether or not it is the blood vessel region by a maximum matching degree that is highest in the matching degrees respectively corresponding to the plurality of templates.

6. The endoscope system according to claim 1,
wherein the blood vessel region determination processor includes a plurality of templates having a plurality of linear shapes in which extension directions of straight lines are different from each other, as the shape featuring the blood vessel, and
the blood vessel region determination processor is configured to obtain a matching degree representing a degree of correlation between a shape of an examination target area of the image and each of the linear shapes of the plurality of templates and to use the highest matching degree in the matching degrees respectively corresponding to the plurality of templates, as the certainty of the blood vessel region in the examination target area.

7. The endoscope system according to claim 5,
wherein each of the templates is configured of pixels having a predetermined size and a rectangular shape, and each of the pixels of each of the templates is a spatial filter having a pixel value set in conformance to the shape, and
the blood vessel region determination processor is configured to associate a pixel in the examination target area of the image with each pixel of the spatial filter and to obtain the matching degree on the basis of a value in which a pixel value of the pixel in the examination target area of the image and a pixel value of a corresponding pixel of the spatial filter are multiplied and added up.

8. The endoscope system according to claim 1,
wherein the evaluation value generation processor is configured to perform the digitization processing with respect to each of the pixels of the image of the biological tissue and to prepare a color map image to which a color is applied in accordance with the pixel evaluation value obtained by the digitization processing,
the blood vessel region determination processor is configured to extract the blood vessel region by obtaining the certainty of the blood vessel region with a spatial filter having a pixel value corresponding to a linear shape, with respect to the image configured of an image evaluation value, and
the integration processor is further configured to prepare a blood vessel removal color map image by using an image in which the blood vessel region is removed from the image configured of the pixel evaluation value and to transmit the blood vessel removal map image along with the inflammation evaluation value to be displayed on the monitor.

9. The endoscope system according to claim 1,
wherein the color component of the image includes a red component, a green component, and a blue component, and
the evaluation value calculation processor is configured to calculate the pixel evaluation value on the basis of a deviation angle deviating with respect to a reference axis set in advance, in which in a color space that is defined by the red component, the blue component, or the green component, a direction of a line segment connecting a reference point set in the color space and a pixel corresponding point corresponding to the color component of each of the pixels of the image passes through the reference point.

* * * * *